(12) United States Patent
Al-Zuhair et al.

(10) Patent No.: US 11,060,120 B1
(45) Date of Patent: Jul. 13, 2021

(54) METHOD OF PRODUCING BIODIESEL FROM MICROALGAE USING THERMO-RESPONSIVE SWITCHABLE SOLVENT

(71) Applicant: UNITED ARAB EMIRATES UNIVERSITY, Al Ain (AE)

(72) Inventors: Sulaiman Abdulrazak Al-Zuhair, Al Ain (AE); Mukhtar Ahmed Ismail, Al Ain (AE)

(73) Assignee: UNITED ARAB EMIRATES UNIVERSITY, Al Ain (AE)

( * ) Notice: Subject to any disclaimer, the term of this patent is extended or adjusted under 35 U.S.C. 154(b) by 0 days.

(21) Appl. No.: 17/105,465

(22) Filed: Nov. 25, 2020

(51) Int. Cl.
*C12P 7/64* (2006.01)
*C10L 1/19* (2006.01)
*B01D 11/04* (2006.01)
*C12N 1/12* (2006.01)

(52) U.S. Cl.
CPC .......... *C12P 7/649* (2013.01); *B01D 11/0492* (2013.01); *C10L 1/19* (2013.01); *C12P 7/6463* (2013.01); *C10L 2200/0476* (2013.01); *C12N 1/12* (2013.01)

(58) Field of Classification Search
CPC ....... C12P 7/649; C12P 7/6463; C12P 7/6436; C10L 1/19
See application file for complete search history.

(56) References Cited

U.S. PATENT DOCUMENTS

| 8,450,111 B2 * | 5/2013 | Salvo ................ C07H 1/08 435/390 |
| 8,513,464 B2 | 8/2013 | Jessop et al. |
| 2011/0217777 A1 * | 9/2011 | Teixeira ............. C12M 47/10 435/410 |

FOREIGN PATENT DOCUMENTS

| CN | 108201773 A | 6/2018 |
| KR | 2018-0095999 A | 8/2018 |
| WO | WO 2016012116 | * 1/2016 |

OTHER PUBLICATIONS

Mariam Al-Ameri, Sulaiman Al-Zuhair, "Using switchable solvents for enhanced, simultaneous microalgae oil extraction-reaction for biodiesel production" Biochemical Engineering Journal 141 (2019) 217-224 (Year: 2019).*
Sigma Aldrich "L4777" 2 pgs accessed Feb. 13, 2021 (Year: 2021).*
Veillette et al., "Production of Biodiesel from Microalgae," Advances in Chemical Engineering, 23, Mar. 2012.
Passos et al, "Thermoreversible (Ionic-Liquid-Based) Aqueous Biphasic Systems," Scientific Reports, vol. 6, No. 04., Feb. 4, 2016, pp. 1-7.
Al-Ameri et al., "Using switchable solvents for enhanced, simultaneous rnicroalgae oil extraction-reaction for biodiesel production," Biochemical Engineering Journal, vol. 141, Jan. 15, 2019, pp. 217-224.
Ismail et al., "Thermo-responsive switchable solvents for simultaneous microalgae cell disruption, oil extraction-reaction, and product separation for biodiesel production," Biocatalysis and Agricultural Biotechnology, vol. 26, May 28, 2020.
Galiwango, E., Ismail, M., Ahmad, M. S., & Al-Zuhair, S. (2020). Effect of thermo-responsive switchable solvents on microalgae cells' disruption and non-isothermal combustion kinetics, Biomass Conversion and Biorefinery, 1-14.
Halim, R., Danquah, M. K., & Webley, P. A. (2012). Extraction of oil from microalgae for biodiesel production: A review. Biotechnology advances, 30(3), 709-732.
Du, Y., Schuur, B., Kersten, S. R., & Brilman, D. W. (2016). Microalgae wet extraction using N-ethyl butylamine for fatty acid production. Green Energy & Environment, 1(1), 79-83.
Ismail, "Thermoresponsive Switchable Solvents for Enhanced, Simultaneous Microalgae Oil Extraction Reaction for Biodiesel Production", Mechanical Engineering Theses 9 (2019), published online at scholarworks.uaeu.ac.ae/mechan_theses/9.

* cited by examiner

Primary Examiner — Thane Underdahl
(74) Attorney, Agent, or Firm — Nath, Goldberg & Meyer; Richard C. Litman

(57) ABSTRACT

The method for producing biodiesel from microalgae using a thermo-responsive switchable solvent includes mixing a thermo-responsive switchable solvent (TSS) in a hydrophilic state with microalgae at room temperature (25° C.); maintaining the TSS-microalgae mixture in the hydrophilic state for a cell disruption time period; raising the temperature of the TSS-microalgae mixture to switch the TSS solvent to a hydrophobic state; maintaining the TSS solvent in the hydrophobic state in the presence of immobilized lipase catalyst and methanol for an extraction/reaction time period to obtain fatty acid methyl esters (FAMEs) as the oils are extracted; lowering the temperature of the TSS-microalgae mixture to switch the TSS solvent back to the hydrophilic state; and maintaining the TSS solvent in the hydrophilic state for a product separation time period. The method may further include extracting the FAMEs from the TSS-microalgae mixture with a nonpolar organic solvent to obtain the biodiesel product.

16 Claims, 8 Drawing Sheets

METHOD OF PRODUCING BIODIESEL FROM MICROALGAE USING THERMO-RESPONSIVE SWITCHABLE SOLVENT

BACKGROUND

1. Field

The disclosure of the present patent application relates to a biodiesel production, and particularly to a method for producing biodiesel from microalgae using a thermo-responsive switchable solvent that provides for cell disruption, simultaneous extraction-reaction, and product separation.

2. Description of the Related Art

Biodiesel is a renewable and sustainable replacement to petroleum diesel and can be directly used in conventional diesel engines without modification. Lipases, fat hydrolyzing enzymes, act well on the high free fatty acid content of the unrefined feedstock under mild conditions, allow easy product separation, and can be retained and reused if immobilized. Hydrophobic solvents reduce mass transfer resistance and deactivation of immobilized lipases due to by-product glycerol. While hydrophobic organic solvents improve enzymatic activity of immobilized lipases, biodiesel production using organic solvents is undesirable, since most organic solvents are volatile and toxic, and therefore hazardous and difficult to separate from the final product. Hydrophobic ionic liquids (ILs) may be a greener alternative to organic solvents for use in biodiesel production due to their negligible vapor pressure and lower toxicity.

Microalgae presents a potential feedstock for biodiesel production due its high lipid content, high growth rate and ability to grow in seawater. Conventional biodiesel production from microalgae is a multistep process, including harvesting, drying, oil extracting, converting extracted oils into biodiesel, and purifying and separating the product. Drying cultivated microalgae cells is a pre-requisite before oil extraction given existing technology. The drying process can be time-consuming and/or energy intensive, expensive, and can cause degradation of thermo-sensitive compounds. Dry or wet, the tough cell wall of microalgae must be disrupted to let the extracting solvent reach and dissolve the oils. Conventional cell disruption methods are energy intensive, expensive, and subject the biomass to harsh conditions that may affect fragile molecules.

Although hydrophobic solvents are suitable to dissolve the oils, they are incapable of disrupting the microalgae cell wall structure. Hydrophilic ILs, on the other hand, effectively dissolve cellulose and hemicellulose that substantially make up cell walls, but are not suitable for oil extraction or as biodiesel reaction media. Therefore, microalgae-to-biodiesel multi-step processes require different solvents of different hydrophobicity for cell disruption, extraction-reaction and product separation. Further, each solvent must be completely removed before the next solvent is added and the next step is carried out, rendering the process energy intensive, economically unfavorable, and environmental wasteful.

Switchable solvents (SSs), unlike conventional solvents, have reversibly changeable physical properties, such as polarity and hydrophobicity. As such, switchable solvents have potential to be used as extractors, reaction media, and product separators. For example, passing $CO_2$ through a hydrophobic 1,8-diazabicyclo-[5.4.0]-undec-7-ene (DBU)-alcohol mixture can transform the DBU-alcohol mixture to a hydrophilic IL consisting of DBUH þ and $RCO_3$— ions. The transformation can be reversed by exposure to $N_2$. Some secondary amines, such as N-ethylbutylamine (EBA) and dipropylamine (DPA), and tertiary amines, such as N,N-dimethylcyclohexylamine (DMCHA), have also been shown to function as SSs when treated with $CO_2$. In their polar state, SSs are suitable for cell disruption, whereas in nonpolar state, their high affinity towards lipids makes them suitable for oils extraction. Simultaneous extraction-reaction of oil from wet, undisrupted microalgae paste was achieved using a 1:1 EBA-water system (for *Neochloris oleoabundans*). However, the system was ineffective for biodiesel production, and the main reason for the low FAME (fatty acid methyl esters, the primary constituent of biodiesel, usually produced by transesterification of vegetable oils with methanol) yield was the excessive use of water that promoted the hydrolysis of the extracted oils rather than transesterification.

$CO_2$-triggered SSs have been used for cell wall disruption, oil extraction, and product separation with varying degrees of success, depending on the particular $CO_2$-triggered SSs used. However, the addition of gases necessitates use of a reflux condenser to avoid evaporation of other reactants, such as methanol. Similar to $CO_2$-triggered SSs, some solvent/IL mixtures, referred to as Thermo-responsive Switchable Solvents (TSS), display an upper critical solution temperature (UCST) or a lower critical solution temperature, at which they switch their affinity to water. For example, polypropylene glycol (PPG)-IL forms an aqueous biphasic system consisting of a hydrophilic IL phase and a hydrophobic PPG phase at low temperatures. Hydrogen bonding between PPG and water molecules initiates this phase separation by overcoming the entropy of a monophasic solution. At high temperatures, these hydrogen bonds are broken, and a monophasic solution is formed. PPG-IL has been used for separation and purification of biomolecules, such as proteins and organelles, from microalgae cells.

Thus, a method for producing biodiesel from microalgae using a thermo-responsive switchable solvent solving the aforementioned problems is desired.

SUMMARY

The method for producing biodiesel from microalgae using a thermo-responsive switchable solvent includes mixing a thermo-responsive switchable solvent (TSS) in a hydrophilic state with microalgae at room temperature (25° C.); maintaining the TSS-microalgae mixture in the hydrophilic state for a cell disruption time period to render oils (the oils are triacylglycerides consisting of three fatty acid molecules connected to a glycerol molecule by ester linkages) in the microalgae accessible for extraction; raising the temperature of the TSS-microalgae mixture to switch the TSS solvent to a hydrophobic state; maintaining the TSS solvent in the hydrophobic state in the presence of immobilized lipase catalyst and methanol for an extraction/reaction time period for simultaneously extracting the oils from the microalgae and reacting the oils with the methanol in a transesterification reaction to obtain fatty acid methyl esters (FAMEs) as the oils are extracted; lowering the temperature of the TSS-microalgae mixture to switch the TSS solvent back to the hydrophilic state; and maintaining the TSS solvent in the hydrophilic state for a product separation time period to separate the FAMEs from the TSS solvent for use as biodiesel. The method may further include extracting the FAMEs from the TSS-microalgae mixture with a nonpolar organic solvent to obtain the biodiesel product.

These and other features of the present subject matter will become readily apparent upon further review of the following specification.

BRIEF DESCRIPTION OF THE DRAWINGS

Similar reference characters denote corresponding features consistently throughout the attached drawings.

DETAILED DESCRIPTION OF THE PREFERRED EMBODIMENTS

Figure 1:
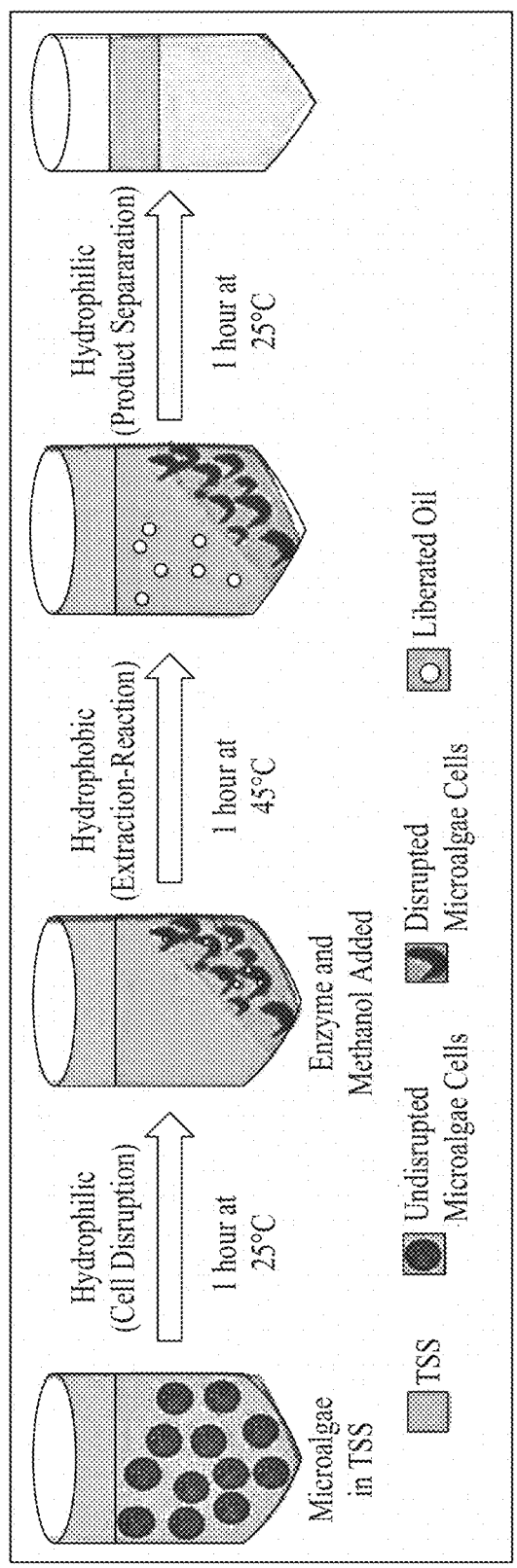
FIG. 1 is a schematic drawing showing steps in a method for producing biodiesel from microalgae using a thermo-responsive switchable solvent.

The method for producing biodiesel from microalgae using a thermo-responsive switchable solvent includes mixing a thermo-responsive switchable solvent (TSS) in a hydrophilic state with microalgae at room temperature (25° C.); maintaining the TSS-microalgae mixture in the hydrophilic state for a cell disruption time period to render oils (the oils are triglycerides consisting of three fatty acid molecules connected to a glycerol molecule by ester linkages) in the microalgae accessible for extraction; raising the temperature of the TSS-microalgae mixture to switch the TSS solvent to a hydrophobic state; maintaining the TSS solvent in the hydrophobic state in the presence of immobilized lipase catalyst and methanol for an extraction/reaction time period for simultaneously extracting the oils from the microalgae and reacting the oils with the methanol in a transesterification reaction to obtain fatty acid methyl esters (FAMEs) as the oils are extracted; lowering the temperature of the TSS-microalgae mixture to switch the TSS solvent back to the hydrophilic state; and maintaining the TSS solvent in the hydrophilic state for a product separation time period to separate the FAMEs from the TSS solvent for use as biodiesel. The method may further include extracting the FAMEs from the TSS-microalgae mixture with a nonpolar organic solvent to obtain the biodiesel product. FIG. 1 shows the steps in the method schematically.

The TSS solvent may be mixed with microalgae that is still wet after harvesting, or after the microalgae has been dried. By performing the method on wet microalgae, the time-consuming (for sun drying) or expensive energy-based (for spray drying) drying step can be omitted, together with consequent loss of thermo-sensitive compounds. It has been estimated that elimination of the drying step may result in a 25% reduction in energy consumption.

In the examples that follow, the TSS used to illustrate the method is a mixture of N,N-diethyl-N-methylammonium methane sulfonate $[N_{1220}]$ $[C_1SO_3]$, polypropylene glycol (PPG), and distilled water. However, it is anticipated that other protic ionic liquids (PILs) may be used to form the TSS, including N,N-dimethyl-N-ethylammonium acetate, $[N_{1120}]$ $[C_1CO_2]$; N,N-dimethyl-N—(N',N'-dimethylaminoethyl)ammonium acetate, $[N_{11[2(N110)]0}]$ $[C_1CO_2]$; N,N-dimethyl-N—(N',N'dimethylaminoethyl) ammonium chloride, $[N_{11[2(N110)]0}]Cl$; N,N-dimethyl-N-ethylammonium phenylacetate, $[N_{1120}]$ $[C_7H_7CO_2]$; and N,N-dimethyl-N—(N',N'dimethylaminoethyl) ammonium octanoate, $[N_{11[2(N110)]0}]$ $[C_7CO_2]$.

The method for producing biodiesel from microalgae using a thermo-responsive switchable solvent will be better understood with reference to the following examples in which the method is compared to a prior art method using a $CO_2$-triggered (but not thermo-responsive) switchable solvent. The following materials were used in the examples that follow. 1,8-Diazabicyclo[5.4.0]undec-7-ene 98% (DBU), Mono-ethanolamine (MEA) ≥98.0%, 1-hexanol anhydrous 99%, PPG 400, n-hexane, and chloroform were purchased from Sigma-Aldrich, USA. N,N-Diethyl-N-methylammonium methane sulfonate, $[N_{1220}][C_1SO_3]$ with a purity of 98%, was obtained from IO-LI-TEC, Germany. Analytical grade methanol with a purity of ≥99% was obtained from Fisher chemicals, USA. Hydrogen, zero air (ultra-pure), helium, carbon dioxide, and nitrogen were supplied by Sharjah Oxygen Company, UAE. Lipase immobilized on acrylic resin (Novozyme®435; activity 11,900 PLU/g) was a kind gift from Novozymes, Denmark. A standard solution of high purity FAMEs mix consisting of 4% myristic acid (C14:0), 10% palmitic acid (C16:0), 6% stearic acid (C18:0), 25% oleic acid (C18:1n9c), 10% Elaidic acid (C18:1n9t), 34% linoleic acid (C18:2n6c), 2% linolelaidic acid (C18:2n6t), 5% linolenic acid (C18:3), 2% arachidonic acid (C20:0), and 2% of behenic acid (C22:0) was purchased from Sigma-Aldrich, USA.

Example 1

Synthesis of $CO_2$-Triggered Switchable Solvents (SSs)

The $CO_2$-triggered switchable solvents (SSs) were DBU-based SSs, namely [DBU] [Hexanol] and [DBU] [MEA], and were prepared as reported previously (Jessop, P. G., et al. (2005). Nature, 436(7054), 1102-1102; Anugwom, I., et al. (2014). *Chem Sus Chem*, 7(4), 1170-1176. Briefly, DBU and 1-hexanol or MEA were mixed in equimolar ratio and stirred vigorously for 5 min, resulting in a hydrophobic solution. An additional $CO_2$-triggered SS comprising EBA mixed with hydrophobic alcohol or amine was also prepared. The $CO_2$-triggered SSs were used by bubbling with $CO_2$ to turn the solvent into the hydrophilic ionic liquid state and returned to the hydrophobic state by stripping the $CO_2$ by the addition of $N_2$.

Example 2

Synthesis of Thermo-Responsive Switchable Solvent (TSS)

Figure 3A:
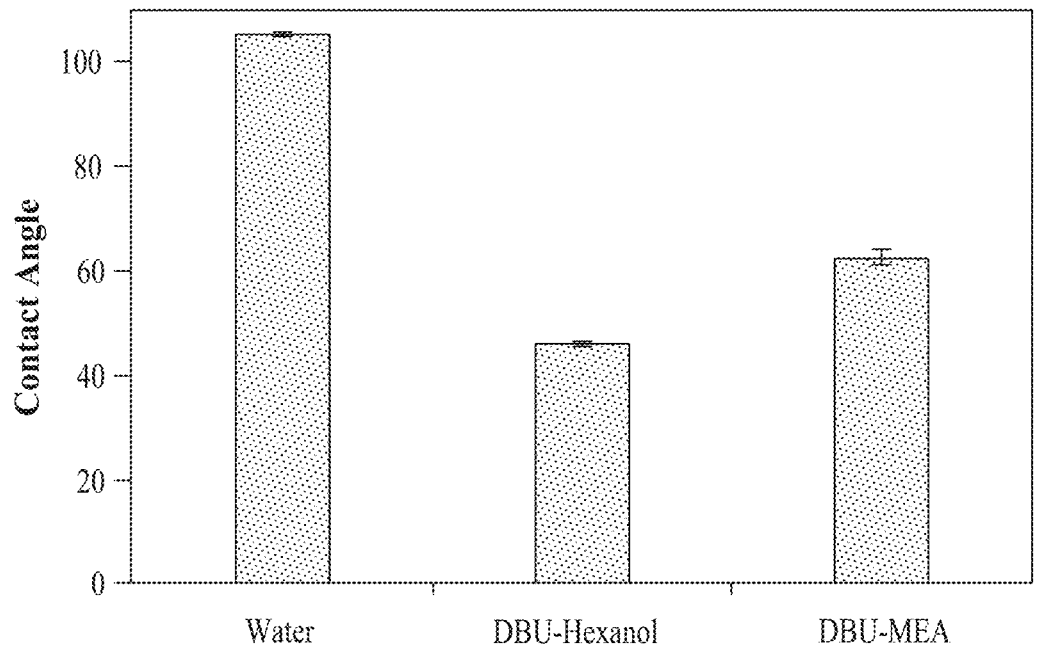
FIG. 3A is a plot of contact angle measurements on a hydrophobic surface, using water as a reference, for exemplary $CO_2$-triggered switchable solvents, DBU-Hexanol SS and DBU-MEA SS, in their hydrophobic form.

The TSS was prepared as described in Passos, H., et al. (2016). *Scientific reports*, 6(1), 1-7. Briefly, a homogeneous mixture, composed of 6 wt. % $[N_{1220}][C_1SO_3]$, 30 wt. % PPG, and 64 wt. % distilled water was prepared at room temperature. This composition, which switches hydrophobicity at 45° C., as reported in Passos et al., was determined to be suitable for enzyme reaction and was selected for this example. However, it is expected that other compositions with varying critical temperatures may also be adapted for the present method. The hydrophobicity of the as-prepared SSs and TSS were evaluated from the surface contact angle. Briefly, a 0.5 µl drop was placed on a hydrophobic surface made of glass laminated with wax paper (Falcon wax paper, UAE), and the contact angle was determined using a contact-angle instrument (Kyowa, drop master series, Japan). The contact angle of a droplet of water was used as a reference. See FIGS. 3A and 3B.

Example 3

Preparation of Microalgae

Freshwater microalgae, *Chlorella* sp., was cultivated in an open pond made of fiberglass (150 cm length, 80 cm width, 30 cm depth) with a horizontal paddlewheel rotating at 1400 rpm/min to mix the culture and run by a single phase electric motor (ML80B4, China). A white fluorescent tube light of 202 µmol/m² s intensity, fixed 35 cm above the culture surface, was programmed to provide 12/12 photoperiod using the 24 h timer. The culture was grown at room temperature in Bold's Basal Medium (BBM), composed of 0.17 mM calcium chloride ($CaCl_2.2H_2O$), 0.43 mM di-potassium hydrogen orthophosphate ($K_2HPO_4$), 0.3 mM magnesium sulphate ($MgSO_4.7H_2O$), 1.29 mM potassium di-hydrogen orthophosphate ($KH_2PO_4$), 8.82 mM sodium nitrate ($NaNO_3$), 0.43 mM sodium chloride (NaCl), and vitamin B12 (0.1% v/v). After 2 weeks, the algal biomass was harvested by centrifugation at 6000 rpm for 5 min using IEC-CL Multispeed centrifuge (Model No. 11210913, France). Dry weight of the biomass was determined by weighing 1 g of wet paste, and measuring the constant weight reached after overnight drying at 70° C.

Example 4

Measurement of Lipid Content

Lipid content was determined using the Bligh and Dyer method. Briefly, the wet harvested microalgae cells were lyophilized overnight (2 h freeze/12 h drying under vacuum) using a freeze dryer (Telstar LyoQuest, Spain) operated at −54° C. and 0.02 mbar. Microalgae oil was extracted from 1 g of lyophilized cells, and homogenized with 15 ml of chloroform-methanol mixture (1:2). The mixture was vigorously mixed using continuous ultrasonication (Branson Sonifier 450, USA) in five cycles of 5 min each to ensure complete cell disruption. Subsequently, the mixture was kept on orbital shaker (Stuart Lab scale Orbital Shaker/SSL1) at room temperature and rotated at 120 rpm for 20 min. Next, 15 ml of chloroform-distilled water mixture (1:2) was added and mixed thoroughly. The mixture was then centrifuged (IEC CL31 multispeed centrifuge, Thermo Scientific, USA) at 1000 rpm for 3 min to separate the biomass. The supernatant was centrifuged again at 2000 rpm for 5 min to separate the two layers and was placed in a separation funnel. The lower chloroform layer containing the extracted oil was collected in a pre-weighed dry beaker and dried in the oven (ULE 400, Memmert Universal) at 60° C. until the chloroform evaporated. The amount of extracted lipid was determined from the difference between the final weight of the dried sample in a beaker and the weight of the empty dry beaker.

Example 5

Comparison of TSS with Organic Solvent and $CO_2$-Triggered SS

Figure 4:
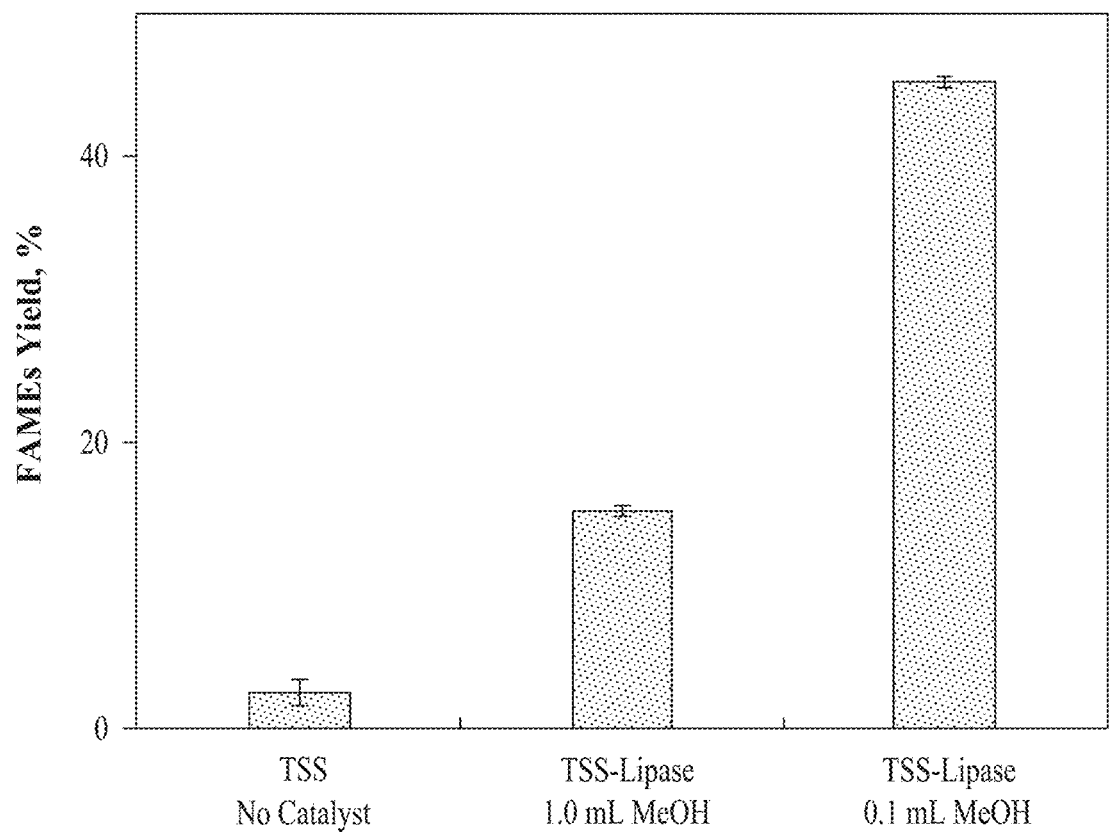
FIG. 4 is a plot of FAME yield in a method for producing biodiesel from microalgae using TSS at 45° C. and 30% enzyme loading with the following solvent program: cell disruption for 1.5 h, extraction/reaction for 1.5 h, and phase separation for 1 h as a function of different quantities of methanol added to the mixture.
Figure 5A:
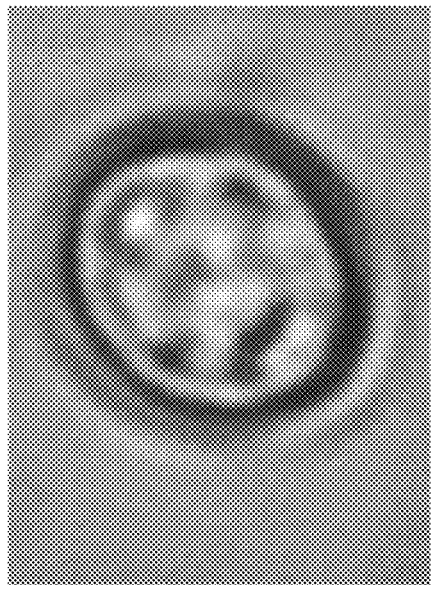
FIGS. 5A and 5C are photomicrographs fresh undisrupted cells of *Chlorella* sp. before exposure to a TSS.
Figure 5B:
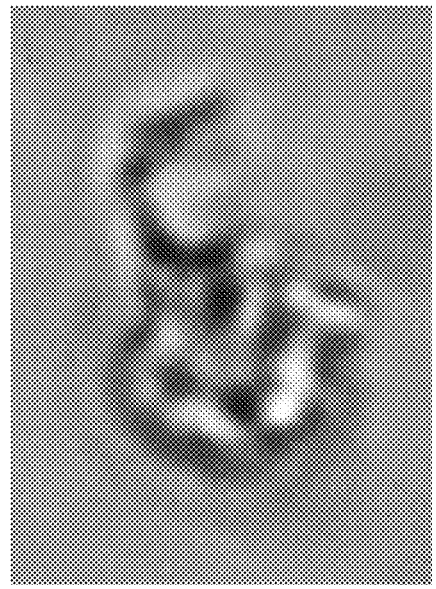
FIGS. 5B and 5D are photomicrographs of the corresponding cells of FIGS. 5A and 5C, respectively, after exposure to a TSS in its hydrophilic state.
Figure 5C:
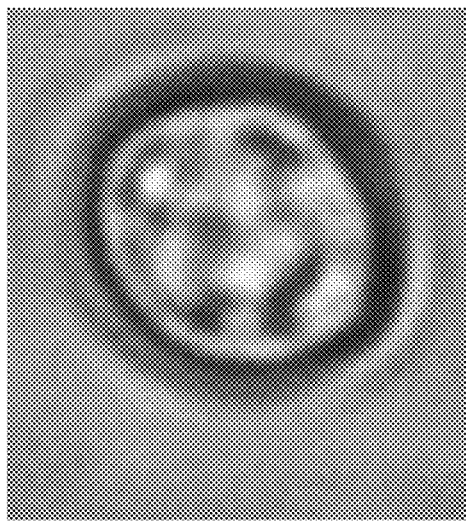
Figure 5D:
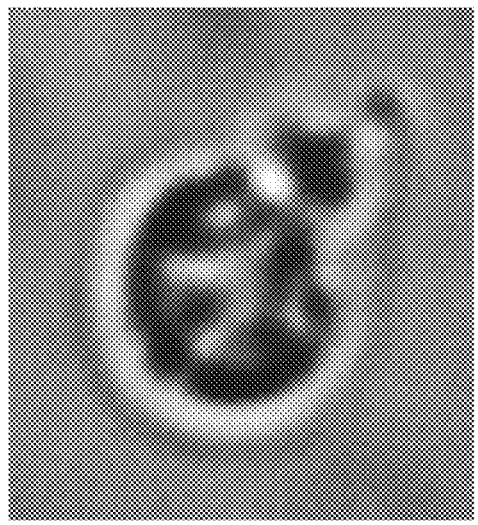

The effectiveness of using TSS to produce biodiesel from microalgae was compared with n-hexane, and $CO_2$-triggered (DBU)-1-hexanol and DBU-MEA. The experimental setup of the TSS tests was much simpler than that of the $CO_2$-triggered amine based SSs. Briefly, a 15 ml capped vial was placed on a hotplate magnetic stirrer (DAIHAN hotplate stirrer, Korea). One gram of wet, undisrupted microalgae paste of predetermined dry content was mixed with immobilized lipase (30 wt % lipase per biomass dry weight), 10 ml TSS, and a pre-specified amount of methanol (specified below regarding experimental procedure and optimization). The system was covered throughout the experiment to minimize the loss of methanol. For the initial screening test, the TSS was maintained hydrophilic for 1.5 h at room temperature, and the reaction contents were continuously stirred to disrupt the cells and liberate the oils. The TSS was switched to hydrophobic state by increasing the temperature to 45° C. and stirred for another 1.5 h to dissolve the liberated oils and simultaneously convert them to biodiesel. Finally, the TSS was switched back to the hydrophilic state by reducing the temperature back to 25° C. to separate the biodiesel. To extract the separated product, 10 ml n-hexane was added to the system and then sent for analysis. The result is shown in FIG. 4. The procedure was repeated in the absence of enzyme for comparison. In addition, running the experiment with n-hexane in place of the exemplary TSS was used as a control.

Figure 2:
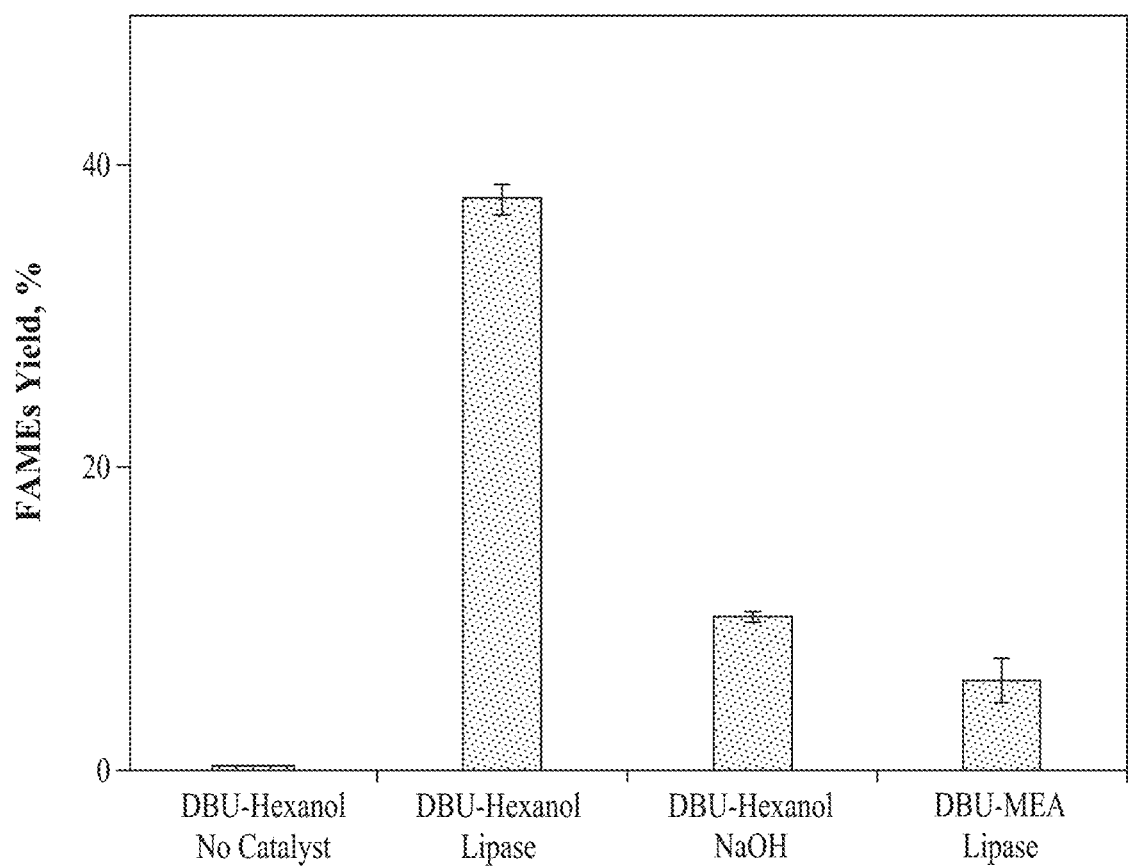
FIG. 2 is a plot of fatty acid methyl esters (FAMEs) yield in a prior art method of using $CO_2$-triggered SSs using 1.0 ml MeOH, 30% enzyme loading and 10 ml SSs, with the following solvent program: cell disruption for 1.5 h, extraction/reaction for 1.5 h, and phase separation for 1 h.

The procedure for evaluating the $CO_2$-triggered amine-based SSs was similar to the one followed for TSS, but required application of gas bubbling to trigger hydrophilicity change. Briefly, a sample of wet, undisrupted microalgae paste (1 g) was mixed with 10 ml of $CO_2$-triggered SS, immobilized lipase (30 wt % lipase per biomass dry weight), and 1.0 ml methanol, and the temperature of the system was maintained at 40° C. The $CO_2$-triggered SS s were turned into hydrophilic ionic liquid by bubbling with $CO_2$ and was kept for 1.5 h for cell disruption. The SS solvent was then turned into hydrophobic by stopping the $CO_2$ bubbling and bubbling with $N_2$ instead. The SS was kept in hydrophobic state for another 1.5 h to facilitate oil extraction and reaction. The SS was turned back to hydrophilic by replacing the $N_2$ bubbling with $CO_2$ bubbling and was kept hydrophilic for 1 h to allow FAMEs separation. The result is shown in FIG. 2.

Example 6

Testing for Reusability of TSS Solvent

Simultaneous extraction-reaction of microalgae lipids was performed to test the reusability of the TSS-immobilized enzyme system for four cycles. In this test, enzyme leaching was avoided by not exposing the enzyme to the TSS in its hydrophilic state at any stage of the reaction. Briefly, 1 g of wet biomass was mixed with 10 ml of the hydrophilic TSS for 1.5 h to allow cell disruption and oil liberation. The solvent was then switched to hydrophobic state to extract the lipids and centrifuged to discard unwanted cell debris. Subsequently, enzymes (30 wt. % loading) and methanol (1.0 ml) were added to initiate the transesterification process and the reaction was carried out for 1.5 h. Before switching the TSS hydrophilic, the enzyme was separated by centrifugation. Subsequently, the solvent was switched to hydrophilic state to separate the FAMEs, which were extracted by adding 10 ml n-hexane. The used enzyme was kept in the refrigerator at 4° C. before reusing in another cycle with 1 g of fresh undisrupted biomass. The steps were repeated for four cycles.

Example 7

Testing Product for Fatty Acid Methyl Esters (FAMEs)

A Gas Chromatograph GC-2010 (Shimadzu, Japan) equipped with a flame ionization detector (FID) and a SP-2380 capillary column (30 m, 0.25 mm, 0.2 μm film thickness) was used to analyze the extracted FAMEs. Helium was used as the carrier gas at a flow rate of 68.9 ml/min. A total of 1 μl sample filtered through a 0.45 μm syringe filter was injected. The temperature of the oven was set at 185° C. and raised to 220° C. after an isothermal time period of 16 min. The temperatures of the injector and detector were set at 220° C., and a divided coefficient of 50 was used. The instrument was calibrated using a standard FAME mix (C14-C22, SIGMA-CRM18917) prepared by dissolving 100 mg of standard FAME mix in 10 mL n-hexane. The amount of the FAMEs produced was presented as a percentage of the total oil in the biomass, calculated according to Eq. 1:

$$FAMEyield = \frac{m_{FAME}}{m_{oil\ content}} \times 100\%. \quad (1)$$

Example 8

Optimization of Method Parameters

Three key parameters were changed to identify their respective effects on simultaneous oil extraction-reaction from wet, undisrupted microalgae using TSS. The tested factors were the TSS solvent program (i.e., cell disruption and extraction-reaction durations) and the amount of methanol. The levels of independent variables based on the results of the experiments are listed in Table 1.

TABLE 1

Levels of independent variables

| Factor | Symbol | Unit | -α | -1 | 0 | 1 | α |
|---|---|---|---|---|---|---|---|
| Cell disruption duration | $x_1$ | h | 0 | 0.5 | 1.5 | 2.5 | 3.0 |
| Extraction-Reaction duration | $x_2$ | h | 0 | 0.5 | 1.5 | 2.5 | 3.0 |
| Methanol Amount | $x_3$ | ml | 0.2 | 0.05 | 0.1 | 0.15 | 0.2 |

Data analysis software (Minitab 2019) was used to develop a central composite design to create a polynomial model between the produced yield (response) and the three parameters (cell disruption, extraction-reaction periods, and the amount of methanol) as shown in Table 2, which shows experimental results using the levels (-α, -1, 0, 1, and α) defined in Table 1.

TABLE 2

Central composite design experiments for the variables of Table 1 and FAMES yield

| Factor | | | Response |
|---|---|---|---|
| $x_1$ | $x_2$ | $x_3$ | FAMEs yield % |
| 0 | 0 | 0 | 43.26 ± 1.15 |
| 0 | 0 | 0 | 42.61 ± 1.72 |
| 1 | -1 | -1 | 36.71 ± 2.75 |
| 1 | -1 | 1 | 49.61 ± 1.75 |
| -1 | 1 | 1 | 76.23 ± 2.42 |
| -1 | -1 | -1 | 18.83 ± 0.24 |
| 1 | 1 | -1 | 50.28 ± 1 |
| 0 | 0 | 0 | 47.11 ± 0.98 |
| 0 | 0 | 0 | 44.94 ± 0.01 |
| -1 | -1 | 1 | 38.03 ± 0.10 |
| -1 | 1 | -1 | 46.34 ± 0.06 |
| 1 | 1 | 1 | 72.64 ± 0.55 |
| -α | 0 | 0 | 33.26 ± 1.10 |
| 0 | 0 | 0 | 45.23 ± 0.37 |
| 0 | 0 | -α | 29.06 ± 2.36 |

TABLE 2-continued

Central composite design experiments for the
variables of Table 1 and FAMES yield

| Factor | | | Response |
|---|---|---|---|
| $x_1$ | $x_2$ | $x_3$ | FAMEs yield % |
| 0 | $-\alpha$ | 0 | 24.48 ± 0.29 |
| 0 | 0 | 0 | 42.63 ± 0.51 |
| 0 | $\alpha$ | 0 | 55.93 ± 0.54 |
| 0 | 0 | $\alpha$ | 50.53 ± 2.87 |
| $\alpha$ | 0 | 0 | 48.46 ± 0.23 |

Figure 7A:
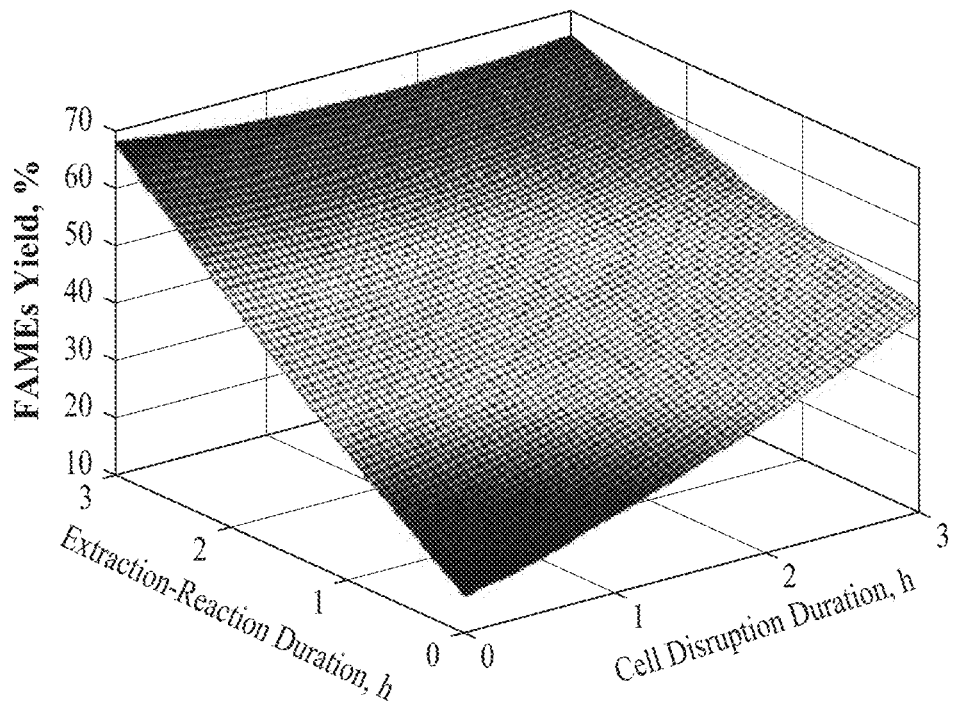
FIG. 7A is a 3-D plot of FAME yield in a method for producing biodiesel from microalgae using a thermo-responsive switchable solvent in the presence of 0.1 ml methanol as a function of varying time periods of cell disruption and extraction-reaction.
Figure 7B:
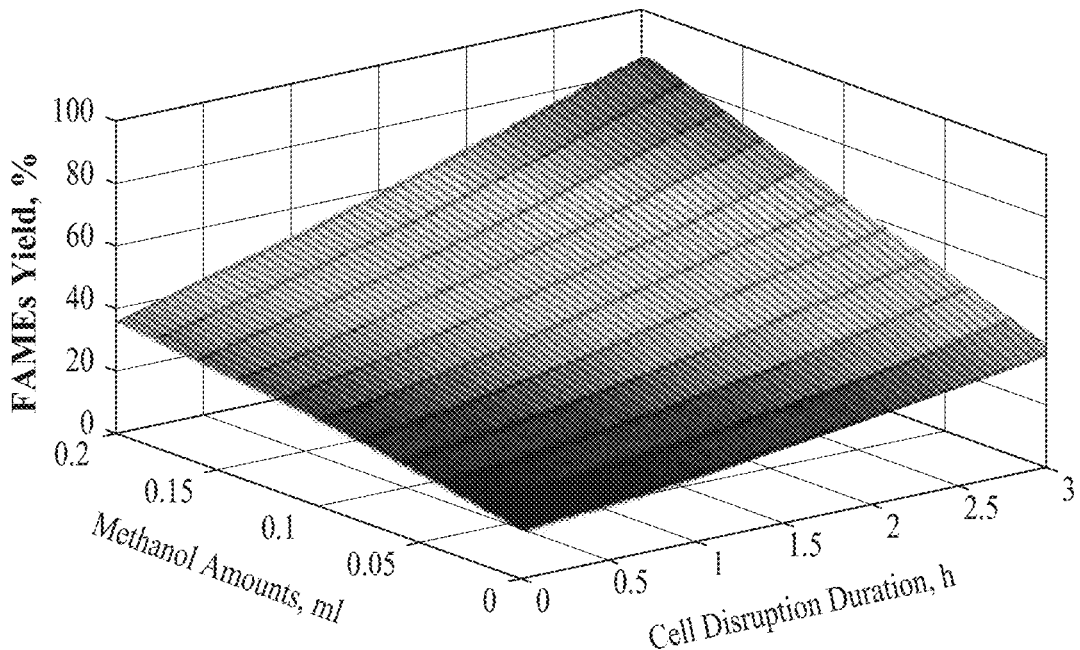
FIG. 7B is a 3-D plot of FAME yield in a method for producing biodiesel from microalgae using a thermo-responsive switchable solvent with a 1.5 h extraction-reaction time period as a function of varying amounts of methanol and varying time periods of cell disruption.
Figure 7C:
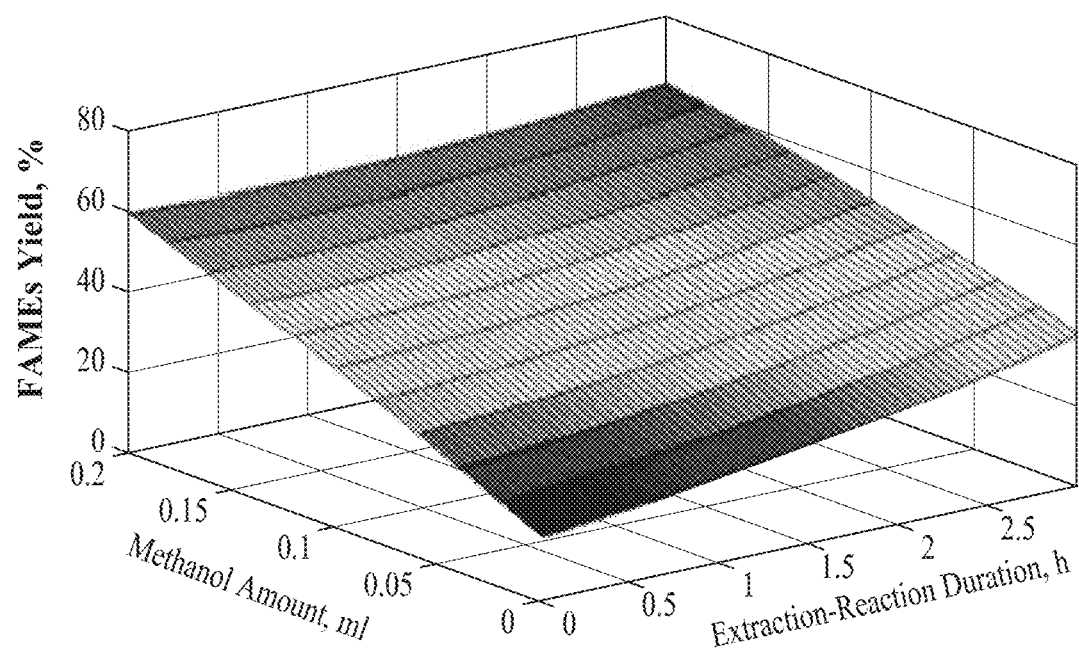
FIG. 7C is a 3-D plot of FAME yield in a method for producing biodiesel from microalgae using a thermo-responsive switchable solvent with a 1.5 h cell disruption time period as a function of varying amounts of methanol and varying time periods of extraction-reaction.

The response surface methodology (RSM) was applied to determine a polynomial, shown in Eq. 2 to express the yield of produced FAMEs as a function of the independent variables. MiniTab 19 statistical software (MiniTab, Inc.) was used for the statistical analysis.

$$Y = a_o + \sum_{i=1}^{3} a_i x_i + \sum_{i=1}^{2} \sum_{j=i+1}^{3} a_{ij} x_i x_j, \quad (2)$$

where Y is the extracted FAMEs yield, and the constants, $a_i$ and $a_{ij}$ are the linear and interaction coefficients, respectively; and $x_i$ and $x_j$ are the independent variables. Three-dimensional surface response plots were generated by varying the two variables within the studied range while holding the third variable constant (see FIGS. 7A-7C).

Example 9

Using $CO_2$-Triggered Switchable Solvents for Biodiesel Production

FIG. 2 shows results of FAMEs production using the $CO_2$-triggered SSs under various conditions. In particular, the above procedure was performed in DBU-Hexanol solvent without enzyme or alkaline catalyst, with immobilized enzyme (lipase-Novozyme 435), with alkaline catalyst (NaOH), and for DBU-MEA solvent with immobilized lipase enzyme catalyst. Enzyme and/or alkaline catalyst are evidently required for efficient FAMEs production, as the lack of both produced almost no FAMEs. Performing the reaction in the presence of NaOH as a catalyst resulted in 10.05±0.32% FAMEs. Addition of Lipase instead of NaOH produced superior results of 37.77±0.32% FAMEs. Alkaline catalysts have drawbacks, e.g., soap formation, so the immobilized enzyme produces higher FAMEs yields and avoids such drawbacks. Another $CO_2$-triggered SS, DBU-MEA, was also tested for FAMEs production in the presence of lipase, showing much lower yield. This is likely due to the lower hydrophobicity of DBU-MEA relative to DBU (see the contact angles in FIG. 3A).

For both tested $CO_2$-triggered SSs, and $CO_2$-triggered SSs in general, the need to bubble the system with gases and to alternate between different gases complicates the process, making scaling up difficult. In addition, losing some amount of the methanol with the vented gasses is inevitable, and the need for a reflex condenser to eliminate methanol evaporation further complicates the process.

Example 10

Using TSS Solvent for Biodiesel Production from Wet Undisrupted Microalgae Cells An exemplary TSS was prepared, composed of 6 wt % $[N_{1220}] [C_1SO_3]$, 30 wt % PPG, and 64 wt % distilled water, and tested for its ability to produce biodiesel.

Figure 3B:
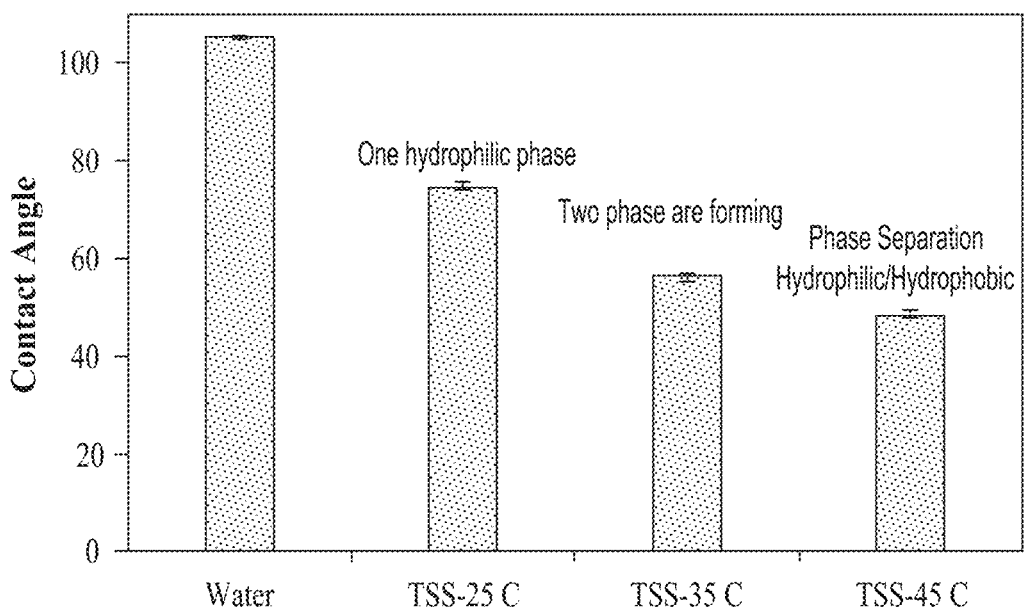
FIG. 3B is a plot of contact angle measurements on a hydrophobic surface, using water as a reference, for exemplary TSS at different temperatures.

Firstly, the hydrophobicity changes of the TSS were evaluated by measuring the contact angle at different temperatures (see FIG. 3B). The TSS-water system formed a hydrophilic miscible solution at room temperature (25° C.), which was confirmed by the high contact angle of 75.1°. As temperature was increased to 35° C., the TSS-water solution formed a cloudy, biphasic system, and the contact angle dropped to 56.3°. Finally, at 45° C., a clear layer was formed, and the contact angle dropped to 48.5°, which was close to that of DBU-hexanol SS in its hydrophobic state.

The exemplary TSS was used for simultaneous lipid extraction-reaction with wet and undisrupted microalgae. Although the solvent program used was the same, the temperature was different at each stage (hydrophilic cell disruption: 1.5 h at 25° C.; hydrophobic extraction-reaction: 1.5 h at 45° C.; hydrophilic FAMEs separation: 1 h at 25° C.). A blank experiment without catalyst was carried out to assess the catalytic activity in the TSS solvent. As shown in FIG. 4, although the catalyzed reaction in TSS led to a higher yield of FAMEs (2.45±0.95%), than in the $CO_2$-triggered SS solvent, it was still insignificant, indicating that the TSS alone does not result in substantial catalytic capacity. Using Novozyme 435 and methanol at the same levels used previously with the $CO_2$-triggered SSs (FIG. 2) resulted in a FAMEs yield of 15.15±0.36%. Adding less methanol of 0.1 ml increased FAMEs yield significantly (45.2±0.37%). This indicates that just 0.1 ml of methanol is enough to overcome the inhibitory effects of methanol escape in the tightly capped system with the TSS.

TSS in the hydrophilic state effectively disrupts the rigid cell wall of the *Chlorella* sp., as evinced in FIG. 5A-5D, showing results of imaging cells before and after exposure to the TSS. This could be attributed to the protic ionic liquid (PIL) constituent of the TSS, dissociating cellulose in the cell walls and decreasing their thickness, thereby facilitating diffusion of lipids out of the cells.

Although both TSS and $CO_2$-triggered SS provide for simultaneous extraction-reaction of oil from wet, undisrupted microalgae, these results clearly showed that the TSS system has the additional advantage of ease of operation and no need of a reflux condenser, significantly simplifying biodiesel production from microalgae.

Example 11

Optimization of Simultaneous Oil Extraction-Transesterification System Using TSS The duration of cell disruption, the duration of extraction-reaction, and the amount of methanol used as a reactant were varied to optimize the simultaneous lipid extraction and transesterification. The ranges of these independent parameters are given in Table 1. The lipid content in the tested conditions was determined to be 8.56±1.56%, using a chloroform:methanol (2:1) solvent mixture. All subsequent FAME yields with respect to the total lipid content were determined as per Eq. 1, above.

Figure 6A:
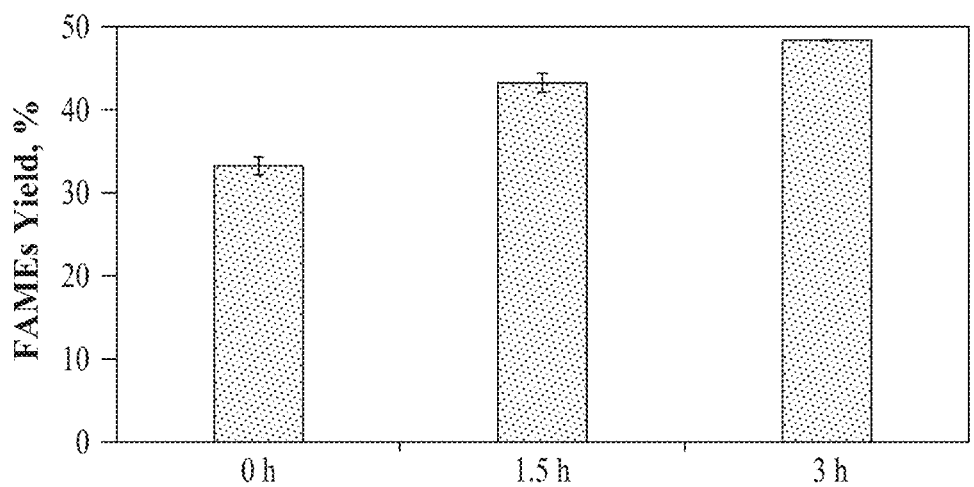
FIG. 6A is a plot comparing FAME yields in a method for producing biodiesel from microalgae using a thermo-responsive switchable solvent wherein the cell disruption time period is 0 h, 1.5 h, and 3 h, respectively, with an extraction-reaction time period of 1.5 h with 0.1 ml methanol and 30% enzyme loading.

The effect of cell disruption in TSS was examined by altering the duration of cell disruption, while the extraction-reaction duration (1.5 h) and the methanol amount (0.1 ml) were kept constant. As shown in FIG. 6A, the yield of FAMEs increased with increasing the duration of cell disruption (from 33.25±1.09% at 0 h to 48.46±0.23% at 3 h). The increase in FAMEs yield is presumably due to the longer exposure to the PILs (protic ionic liquids) present in the TSS, which eventually enhances lipid extraction. Similar results have been reported for $CO_2$-triggered SSs used for simultaneous cell disruption and extraction-reaction using the same microalgae strain as presently tested.

Figure 6B:
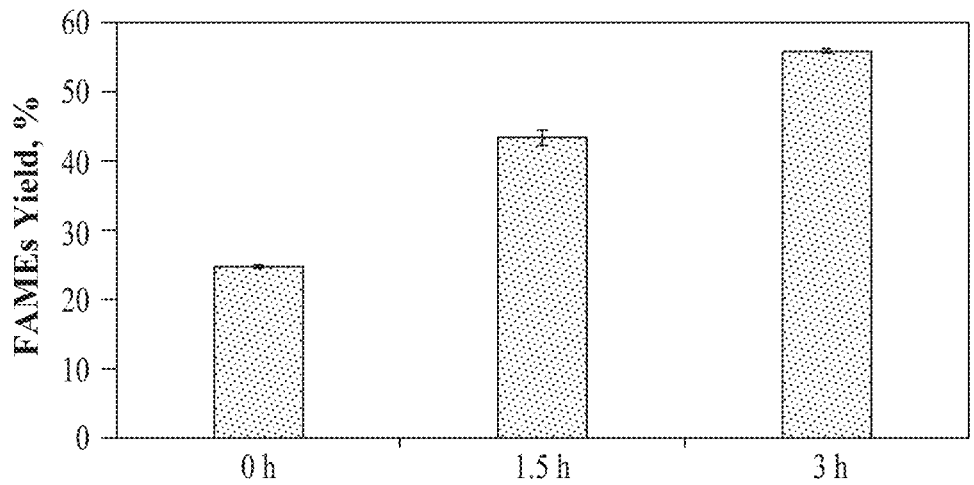
FIG. 6B is a plot comparing FAME yields in a method for producing biodiesel from microalgae using a thermo-responsive switchable solvent wherein the extraction-reaction time period is 0 h, 1.5 h, and 3 h, respectively, with a cell disruption time period of 1.5 h with 0.1 ml methanol and 30% enzyme loading.

Next, the duration of extraction-reaction was altered, while the cell disruption duration (1.5 h) and the methanol amount (0.1 ml) were kept constant. As shown in FIG. 6B, the FAMEs yield increased with increasing duration of the extraction-reaction (from 24.47±0.29% at 0 h to 55.93±0.53% at 3 h). The exemplary TSS was more effective for extraction-reaction compared to the $CO_2$-triggered SS, and hence achieved better FAME yield in less time.

Figure 6C:
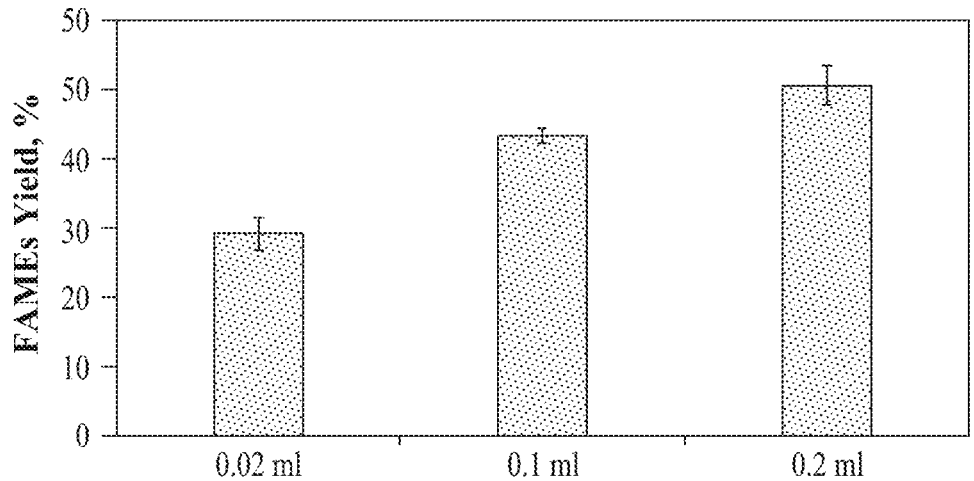
FIG. 6C is a plot comparing FAME yields in a method for producing biodiesel from microalgae using a thermo-responsive switchable solvent wherein the cell disruption time period and the extraction-reaction time period are each 1.5 h with 0.02 ml, 0.1 ml, and 0.2 ml methanol, respectively, and 30% enzyme loading.

Finally, the methanol amount used in the reaction was varied in the range of 0.02-0.2 ml, while cell disruption and extraction-reaction durations were kept constant at 1.5 h each. As shown in FIG. 6C, the increase in FAMEs yield was directly proportional to the increase in the methanol amount used (from 25.06±2.36% at 0.02 ml to 50.53±2.87% at 0.2 ml). Interestingly, while increasing methanol amount from 0.02 to 0.1 ml increased the yield by 73%, a further increase to 0.2 ml increased the yield by just 17%. In fact, at higher amounts, methanol inhibited the reaction (see FIG. 4).

Regression analysis was performed on the experimental data shown in Table 2. A second order regression interactive model was developed relating the FAMEs yield (Y) and the three independent parameters of cell disruption duration $x_1$, extraction-reaction duration $x_2$, and methanol amount $x_3$. All studied parameters were significant (P-value<0.05), but the quadratic and interaction terms were shown to be insignificant (P-value>0.5), consistent with the linear relationships between FAMEs yield with increasing independent parameters (FIGS. 6A-6C, respectively). The results of the second order regression analysis are shown in Table 3.

TABLE 3

Response Surface Regression: FAMEs yield versus cell disruption duration, extraction-reaction duration and methanol quantity Coded Coefficients

| Term | Coef | SE Coef | T-value | P-value | VIF |
|---|---|---|---|---|---|
| Constant | 45.46 | 2.19 | 20.79 | 0.000 | |
| $x_1$ | 6.07 | 2.36 | 2.58 | 0.028 | 1.06 |
| $x_2$ | 18.49 | 2.36 | 7.85 | 0.000 | 1.06 |
| $x_3$ | 15.19 | 2.57 | 5.92 | 0.000 | 1.02 |
| $x_1^2$ | 2.55 | 3.79 | .67 | .516 | 1.01 |
| $x_2^2$ | 2.08 | 3.79 | .55 | .595 | 1.01 |
| $x_3^2$ | −1.65 | 4.02 | −.41 | .691 | 1.03 |
| $x_1x_2$ | −7.70 | 4.29 | −1.80 | .103 | 1.00 |
| $x_1x_3$ | −4.09 | 5.14 | −.79 | .445 | 1.06 |
| $x_2x_3$ | 6.21 | 5.14 | 1.21 | .255 | 1.06 |

Analysis of Variance

| Source | DF | Adj SS | Adj MS | F-value | P-value |
|---|---|---|---|---|---|
| Model | 9 | 3226.51 | 358.50 | 12.35 | 0.000 |
| Linear | 3 | 2996.29 | 998.76 | 34.42 | 0.000 |
| $x_1$ | 1 | 192.53 | 192.53 | 6.64 | 0.028 |
| $x_2$ | 1 | 1787.48 | 1787.48 | 61.60 | 0.000 |
| $x_3$ | 1 | 1016.27 | 1016.27 | 35.02 | 0.000 |
| Square | 3 | 29.54 | 9.85 | 0.34 | 0.797 |
| $x_1^2$ | 1 | 13.17 | 13.17 | 0.45 | 0.516 |
| $x_2^2$ | 1 | 8.76 | 8.76 | 0.30 | 0.595 |
| $x_3^2$ | 1 | 4.87 | 4.87 | 0.17 | 0.691 |
| 2-way interaction | 3 | 154.37 | 51.46 | 1.77 | 0.216 |
| $x_1x_2$ | 1 | 93.66 | 93.66 | 3.23 | 0.103 |
| $x_1x_3$ | 1 | 18.33 | 18.33 | 0.63 | 00.445 |
| $x_2x_3$ | 1 | 42.37 | 42.37 | 1.46 | 0.255 |
| Error | 10 | 290.18 | 29.02 | | |
| Lack-of-fit | 5 | 274.29 | 54.86 | 17.26 | 0.004 |
| Pure error | 5 | 15.89 | 3.18 | | |
| Total | 19 | 3516.69 | | | |

The developed model is shown in Eq. 3:

$$Y = -0.6 + 9.11x_1 + 9.62x_2 + 190x_3 + 1.13x_1x_1 + 0.92x_2x_2 - 203x_3x_3 - 3.42x_1x_2 - 30.3x_1x_3 - 46.0x_2x_3. \quad (3)$$

An optimization process was carried out using the response optimizer in Minitab. The software-calculated optimum conditions were found to be 0.5 h cell-disruption duration at room temperature, 3 h extraction-reaction at 45° C., and 0.15 ml methanol in the reaction system. As the linear effects of the hydrophobic period ($x_2$) and methanol amount ($x_3$) on the yield were the most significant, as shown from the P-values in Table 3, it was expected that the optimum condition be close to the highest value. The linear effect of cell disruption duration ($x_1$), however, was much less significant, and hence the optimization results showed a value somewhere in the middle of the tested values. At these conditions, the FAMEs yield predicted by the model was 78.65%.

An additional independent experiment at the calculated optimal conditions was performed, resulting in an actual FAMEs yield of 75.11±1.03%, which is close to the value predicted by the model. The combined effects of cell disruption duration, extraction-reaction duration and methanol amounts in the system on FAMEs yield are shown as 3D plots in FIGS. 7A-7C. The increase in FAMEs yield was directly proportional to the increase in each of the three parameters, with extraction-reaction duration being the most significant parameter. Further, the increase in yield followed a linear pattern with all the parameters, suggesting that the second order terms were less significant than the linear terms (see Table 3).

Example 12

Reusability of TSS-Enzyme System

Figure 8:
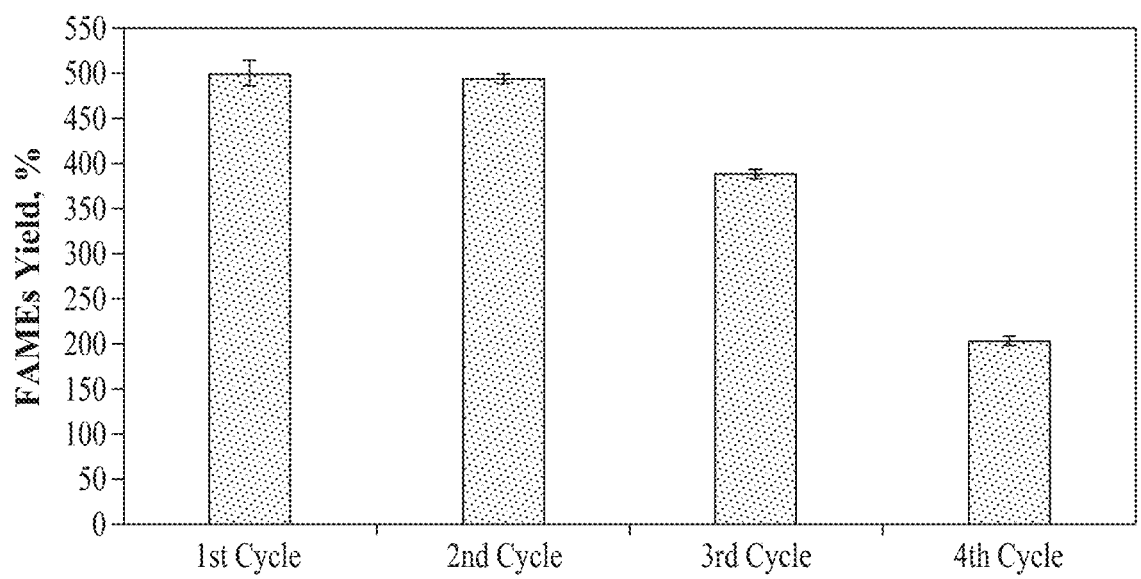
FIG. 8 is a plot of FAME yield in a method for producing biodiesel from microalgae using a thermo-responsive switchable solvent as a function of the number of cycles of reusing the lipase enzyme without washing at 30% enzyme loading and 0.1 ml methanol, with the following solvent program: cell disruption for 1.5 h, extraction/reaction for 1.5 h, and phase separation for 1 h.

The reusability of the TSS-enzyme system was examined for four consecutive cycles using fresh biomass in each cycle. The test was done without washing the enzyme between the cycles. As shown in FIG. 8, stability and reusability were preserved in the second cycle, with a negligible drop in the FAMEs yield. The drop increased in the following cycles, such that the yields of the fourth cycle were approximately 40% those of the first cycle. The drop is presumably mainly due to the deposition of glycerol byproduct over multiple cycles. However, the stability and reusability of the present TSS-enzyme system may be improved by various techniques, such as washing the reaction system with solvent, such as tert-butanol, to remove the deposited glycerol.

The present methods using TSS for cell disruption, oil extraction-reaction and product separation to produce biodiesel from microalgae successfully produces substantial FAMEs yields, in some embodiments enhancing FAMEs yields over methods using $CO_2$-triggered SSs. The TSS-enzyme system described above shows the enzyme catalyst retains its activity for at least two cycles, and is substantially retained over four. Potentially, reusability could be further enhanced by known means, such as glycerol removal, by washing with appropriate solvents. In summary, the present method significantly simplifies the production of biodiesel from microalgae while providing enhanced efficiency.

It is to be understood that the method for producing biodiesel from microalgae using a thermo-responsive switchable solvent is not limited to the specific embodiments described above, but encompasses any and all embodiments within the scope of the generic language of the following claims enabled by the embodiments described herein, or otherwise shown in the drawings or described above in terms sufficient to enable one of ordinary skill in the art to make and use the claimed subject matter.

We claim:

1. A method for producing biodiesel from microalgae using a thermo-responsive switchable solvent, comprising the steps of:
    mixing a thermo-responsive switchable solvent (TSS) in a hydrophilic state with microalgae at room temperature of 25° C.;
    maintaining the TSS-microalgae mixture in the hydrophilic state for a cell disruption time period to render oils in the microalgae accessible for extraction, the oils being triacylglycerides formed from three fatty acids connected to glycerol by ester linkages;
    raising the temperature of the TSS-microalgae mixture to switch the TSS solvent to a hydrophobic state;
    maintaining the TSS solvent in the hydrophobic state in the presence of immobilized lipase catalyst and methanol for an extraction/reaction time period for simultaneously extracting the oils from the microalgae and reacting the oils with the methanol in a transesterification reaction to obtain fatty acid methyl esters (FAMEs) as the oils are extracted;
    lowering the temperature of the TSS-microalgae mixture to switch the TSS solvent back to the hydrophilic state; and
    maintaining the TSS solvent in the hydrophilic state for a product separation time period to separate the FAMEs from the TSS solvent for use as biodiesel.

2. The method for producing biodiesel according to claim 1, further comprising the step of extracting the FAMEs from the TSS-microalgae mixture with a nonpolar organic solvent to obtain the biodiesel product.

3. The method for producing biodiesel according to claim 1, further comprising the step of extracting the FAMEs from the TSS-microalgae mixture with n-hexane extraction solvent to obtain the biodiesel product.

4. The method for producing biodiesel according to claim 1, wherein the TSS is a mixture of propylene glycol, water, and a protic ionic liquid selected from the group consisting of N,N-dimethyl-N-ethylammonium acetate $[N_{1120}]$ $[C_1CO_2]$; N,N-diethyl-N-methylammonium methane sulfonate $[N_{1220}]$ $[C_1SO_3]$; N,N-dimethyl-N—(N',N'dimethylaminoethyl)ammonium acetate, $[N_{11[2(N110)]0}]$ $[C_1CO_2]$; N,N-dimethyl-N—(N',N'dimethylaminoethyl) ammonium chloride, $[N_{11[2(N110)]0}]Cl$; N,N-dimethyl-N-ethylammonium phenylacetate, $[N_{1120}]$ $[C_7H_7CO_2]$; and N,N-dimethyl-N—(N',N'dimethylaminoethyl) ammonium octanoate, $[NN_{11[2(N110)]0}]$ $[C_7CO_2]$.

5. The method for producing biodiesel according to claim 1, wherein the TSS is a mixture of propylene glycol, water, and N,N-diethyl-N-methylammonium methane sulfonate $[N_{1220}]$ $[C_1SO_3]$.

6. The method for producing biodiesel according to claim 1, wherein the TSS is a mixture of 6 wt. % N,N-diethyl-N-methylammonium methane sulfonate $[N_{1220}]$ $[C_1SO_3]$, 30 wt. % PPG, and 64 wt. % distilled water.

7. The method for producing biodiesel according to claim 6, wherein the cell disruption time period is between 0.5 hours and 3 hours.

8. The method for producing biodiesel according to claim 6, wherein the cell disruption time period is 0.5 hours.

9. The method for producing biodiesel according to claim 6, wherein said step of raising the temperature of the TSS-microalgae mixture to switch the TSS solvent to a hydrophobic state comprises raising the temperature of the TSS-microalgae mixture to 45° C. to switch the TSS solvent to a hydrophobic state.

10. The method for producing biodiesel according to claim 6, wherein the extraction-reaction time period is between 0.5 hours and 3 hours.

11. The method for producing biodiesel according to claim 6, wherein the extraction-reaction time period is 3 hours.

12. The method for producing biodiesel according to claim 6, wherein said step of maintaining the TSS solvent in the hydrophobic state in the presence of immobilized lipase catalyst and methanol for an extraction/reaction time period comprises maintaining the TSS solvent in the hydrophobic state in the presence of immobilized lipase catalyst and between 0.02-0.2 ml methanol per gram of microalgae for an extraction/reaction time period.

13. The method for producing biodiesel according to claim 6, wherein said step of maintaining the TSS solvent in the hydrophobic state in the presence of immobilized lipase catalyst and methanol for an extraction/reaction time period comprises maintaining the TSS solvent in the hydrophobic state in the presence of immobilized lipase catalyst and 0.15 ml methanol per gram of microalgae for an extraction/reaction time period.

14. The method for producing biodiesel according to claim 1, wherein said step of mixing a thermo-responsive switchable solvent (TSS) in a hydrophilic state with microalgae at room temperature of 25° C. comprises mixing a thermo-responsive switchable solvent (TSS) in a hydrophilic state with microalgae at room temperature of 25° C. while the microalgae is still in a wet state after harvesting.

15. The method for producing biodiesel according to claim 1, wherein said step of mixing a thermo-responsive switchable solvent (TSS) in a hydrophilic state with microalgae at room temperature of 25° C. comprises mixing a thermo-responsive switchable solvent (TSS) in a hydrophilic state with microalgae at room temperature of 25° C. after the microalgae has been dried.

16. The method for producing biodiesel according to claim 1, wherein said microalgae comprises *Chlorella* sp.

* * * * *